(12) United States Patent
Jain et al.

(10) Patent No.: US 9,604,897 B2
(45) Date of Patent: Mar. 28, 2017

(54) IONIC LIQUID COMPOSITION

(71) Applicant: RELIANCE INDUSTRIES LIMITED, Mumbai, Maharashtra (IN)

(72) Inventors: Suresh Shantilal Jain, Palava (IN); Pavankumar Aduri, Palava (IN); Uday Ratnaparkhi, Maharashtra (IN); Parasu Veera Uppara, Maharashtra (IN)

(73) Assignee: Reliance Industries Limited, Mumbai, Maharashtra (IN)

( * ) Notice: Subject to any disclaimer, the term of this patent is extended or adjusted under 35 U.S.C. 154(b) by 0 days.

(21) Appl. No.: 14/787,963

(22) PCT Filed: Apr. 25, 2014

(86) PCT No.: PCT/IN2014/000269
§ 371 (c)(1),
(2) Date: Oct. 29, 2015

(87) PCT Pub. No.: WO2014/184804
PCT Pub. Date: Nov. 20, 2014

(65) Prior Publication Data
US 2016/0107972 A1    Apr. 21, 2016

(30) Foreign Application Priority Data
May 14, 2013   (IN) .......................... 1722/MUM/2013

(51) Int. Cl.
C07C 51/265    (2006.01)
(52) U.S. Cl.
CPC .................. C07C 51/265 (2013.01)

(58) Field of Classification Search
CPC ................................................... C07C 51/265
See application file for complete search history.

(56) References Cited

U.S. PATENT DOCUMENTS 3,557,173 A  *  1/1971  Trevillyan .............. C07C 51/42
                                                        556/147
7,985,875 B2    7/2011  Hashmi et al.

FOREIGN PATENT DOCUMENTS

| IL | 149339 | * | 3/2008 |
| WO | 2011/010116 A2 | | 1/2011 |
| WO | 2012/012047 A2 | | 1/2012 |
| WO | WO2013001331 | * | 7/2013 |

OTHER PUBLICATIONS

International Search Report of PCT/IN2014/000269, mailed Sep. 26, 2014.
Ji et al, Benzyl-3-methylimidazolium chloride 0.25-hydrate, Acta Crystallographica Section E, Structure Reports Online, vol. 66, Part 1, Jan. 2010.

* cited by examiner

*Primary Examiner* — Paul A Zucker
*Assistant Examiner* — Mark Luderer
(74) *Attorney, Agent, or Firm* — Collard & Roe, P.C.

(57) ABSTRACT

The present disclosure provides a composition for preparing aryl carboxylic acid; said composition comprising: at least one ionic liquid, at least one catalyst, at least one non-oxidizable polar solvent, and at least one oxidizable multi-alkylated arylene compound with no two successive ring positions bearing alkyl group. The present disclosure also provides a process for preparing aryl carboxylic acid.

13 Claims, No Drawings

IONIC LIQUID COMPOSITION

CROSS REFERENCE TO RELATED APPLICATIONS

This application is the National Stage of PCT/IN2014/000269 filed on Apr. 25, 2014, which claims priority under 35 U.S.C. §119 of Indian Application No. 1722/MUM/2013 filed on May 14, 2013, the disclosures of which are incorporated by reference. The international application under PCT article 21(2) was published in English.

FIELD

The present disclosure relates to ionic liquids. Particularly, the present disclosure relates to ionic liquids containing a composition for manufacturing aromatic carboxylic acids such as terephthalic acid.

DEFINITION

In the context of the present disclosure, the term "ionic liquid" means a molecular composition comprising cationic and anionic counterparts interacting with each other by means including but not limited to electrostatic, covalent or semi-covalent bond, and said composition being in a phase including but not limited to liquid, semi-solid, viscous mass or a mixture thereof at a pre-determined temperature and pressure irrespective of the phase of occurrence of said composition at ambient temperature and pressure.

BACKGROUND

Ionic liquids are liquids composed of ions that are fluid around or below 100° C. Ionic liquids, also referred to as room-temperature-molten salts, have potential uses as electrolytes for a variety of electrochemical devices such as lithium secondary batteries, solar cells, actuators, electric double-layer capacitors and the like, reaction media, and catalysts for organic syntheses.

Ionic liquids are also used in a wide variety of applications. Recently, alkyl ionic liquids have been proposed as a promoter in manufacturing aromatic carboxylic acids such as terephthalic acid.

Terephthalic acid is an organic compound with formula $C_6H_4(COOH)_2$. This colourless solid is a commodity chemical, used as a precursor for polyester PET, used to make clothing and plastic bottles. World production in 1970 was around 1.75 million tonnes. By 2006, global purified terephthalic acid (PTA) demand exceeded 30 million tonnes. There is a smaller, but nevertheless significant, demand for terephthalic acid in the production of polybutylene terephthalate and several other engineering polymers.

U.S. Pat. No. 7,985,875 suggests a process for preparing an aromatic carboxylic acid by liquid phase oxidation which comprises contacting a benzene or naphthalene compound having two or three C1-C4 alkyl, hydroxyalkyl or formyl groups with an oxygen-containing gas in the presence of a carboxylic acid solvent, a catalyst and a promoter in a reaction zone, the promoter is an ionic liquid comprising an organic cation selected from the group consisting of 1-alkylpyridinium and 1,3-dialkylimidazolium and an anion consisting essentially of bromide or iodide. However, though the known alkyl ionic liquids act as promoters in manufacturing terephthalic acid, they are not able to reduce the formation of impurities such as 4-carboxy-benzaldehyde (4-CBA).

Reducing 4-CBA impurity in terephthalic acid is very important as 4-CBA acts as a chain terminating agent during the PET polymerization process and hence the desired PET molecular weight may not be achieved.

Accordingly, it is desired to develop ionic liquid/s containing a composition which is capable of solubilizing not only terephthalic acid and 4-CBA, but also various other intermediates and side products, thereby reducing the formation of impurities and producing aromatic carboxylic acids such as terephthalic acid in pure form.

OBJECTS

Some of the objects of the present disclosure, which at least one embodiment herein satisfies, are as follows:

It is an object of the present disclosure to provide a composition containing ionic liquid/s which can act as a co-solvent as well as a promoter in manufacturing terephthalic acid.

It is another object of the present disclosure to provide a composition containing ionic liquids, which is capable of reducing the formation of impurities such as 4-CBA when used in manufacturing aromatic carboxylic acids.

It is another object of the present disclosure to provide a process for the preparation of terephthalic acid in the presence of ionic liquid/s.

It is still another object of the present disclosure to provide a process for the preparation of terephthalic acid which can be carried out in a continuous manner.

It is yet another object of the present disclosure to provide a process for the preparation of terephthalic acid in which the thermo-oxidative loss of the ionic liquid is minimum.

It is a further object of the present disclosure to provide a process for the preparation of terephthalic acid in which the ionic liquid and the catalyst are recovered and recycled.

SUMMARY

In accordance with the present disclosure there is provided a composition for preparing aryl carboxylic acid; said composition comprising:

at least one ionic liquid of formula I, in an amount of 0.05 to 50% of the total mass of the composition;

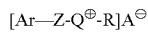            Formula I wherein,
Ar is substituted or un-substituted aryl group,
Z is $(CH_2)_n$, wherein n is an integer from 0 to 10,
$Q^+$ is an organic cation selected from the group consisting of quaternary ammonium, cholinium, sulfonium, phosphonium, guanidinium, imidazolium, pyridinium, pyrrolidinium, morpholinium, quinolinium, isoquinolium, pyrazolium and piperidinium;
R is $C_1$ to $C_{20}$ linear or branched alkyl group or Ar—Z,
$A^-$ is an anion selected from the group consisting of chlorides, bromides, fluorides, iodides, mesylates, tosylates, sulfates, alkyl sulfonatses, phosphates, phosphonates, akyl phosphates, nitrates, nitrites, carbonates, acetates, bicarbonates, hydroxides and oxides;
at least one catalyst, in an amount of 0.01 to 5% of the total mass of the composition;
at least one non-oxidizable polar solvent; and at least one oxidizable multi-alkylated arylene compound with no two successive ring positions bearing alkyl group,
said composition when used in the preparation of aryl carboxylic acid results in the formation of less than 4000 ppm of partially oxidized derivatives of said multi-alkylated arylene compound; said derivatives comprising at least one carboxylic acid moiety and at least one aldehyde moiety.

The proportion of the ionic liquid to the non-oxidizable polar solvent can range between 1:1 and 1:20.

The catalyst can comprise at least one metal compound, the metal being selected from the group consisting of cobalt, magnesium, chromium, copper, nickel, vanadium, iron, molybdenum, tin, cerium, zirconium, cesium and titanium.

The catalyst can be at least one selected from the group consisting of cobalt acetate, manganese acetate, cerium acetate, potassium acetate, cesium acetate, zirconium acetate, copper acetate, cobalt oxalate, manganese oxalate, cerium oxalate, potassium oxalate, cesium oxalate, zirconium oxalate and copper oxalate.

The non-oxidizable polar solvent can be at least one solvent selected from the group consisting of acetic acid, methyl acetate ethyl acetate, propyl acetate, benzyl acetate, and water.

For ionic liquids of formula I, Ar can be phenyl, and Z can be $(CH_2)_n$, wherein n is 1, $Q^+$ is imidazolium group, R is methyl, and $A^-$ is bromide.

The composition can further comprise at least one bromine source selected from the group consisting of HBr, NaBr, KBr, $NH_4Br$, benzylbromide, monobromoacetic acid, di-bromo acetic acid, bromoacetyl bromide, tetrabromomethane and ethylene di-bromide.

The composition can further comprise at least one mono alkyl ionic liquid comprising an organic cation selected from the group consisting of quaternary ammonium, cholinium, sulfonium, phosphonium, guanidinium, imidazolium, pyridinium, pyrrolidinium, morpholinium, quinolinium, isoquinolium, pyrazolium and piperidinium; and an anion selected from the group consisting of chlorides, bromides, fluorides, iodides, mesylates, tosylates, sulfates, alkyl sulfonates, phosphates, phosphonates, akyl phosphates, nitrates, nitrites, carbonates, acetates, bicarbonates, hydroxides and oxides.

The aryl carboxylic acid can be at least one compound selected from the group consisting of terephthalic acid, isophthalic acid, p-toluic acid, m-toluic acid, 4-formyl benzoic acid, 3-formyl benzoic acid, Naphthoic acid, Trimesic acid, benzoic acid, and substituted benzoic acid.

The oxidizable multi-alkylated arylene compound can be at least one selected from the group consisting of para-xylene, meta-xylene, methylnaphthalene, mesitylene, toluene, substituted toluene and combinations thereof.

The partially oxidized derivative can be at least one selected from the group consisting of 4-carboxy benzaldehyde, 3-carboxy benzaldehyde, p-tolualdehyde, m-tolualdehyde, naphthalenecarboxaldehyde, 1,5-dicarboxilic, 3-formyl-benzene, benzaldehyde, substituted benzaldehyde and combinations thereof.

The oxidizable multi-alkylated arylene compound can be para-xylene, the non-oxidizable polar solvent can be acetic acid, the partially oxidized derivative can be 4-carboxy benzaldehyde and the aryl carboxylic acid can be terephthalic acid.

In accordance with another aspect of the present disclosure there is provided a process for obtaining aryl carboxylic acid; said process comprising the following steps:

a. preparing a composition comprising:
at least one ionic liquid of formula I, in an amount of 0.05 to 50% of the total mass of the composition;

$$[Ar—Z-Q^{\oplus}-R]A^{\ominus} \qquad \text{Formula I}$$

wherein,
Ar is substituted or un-substituted aryl group,
Z is $(CH_2)_n$, wherein n is an integer from 0 to 10,
$Q^+$ is an organic cation selected from the group consisting of quaternary ammonium, cholinium, sulfonium, phosphonium, guanidinium, imidazolium, pyridinium, pyrrolidinium, morpholinium, quinolinium, isoquinolium, pyrazolium and piperidinium;
R is $C_1$ to $C_{20}$ linear or branched alkyl group or Ar—Z,
$A^-$ is an anion selected from the group consisting of chlorides, bromides, fluorides, iodides, mesylates, tosylates, sulfates, alkyl sulfonatses, phosphates, phosphonates, akyl phosphates, nitrates, nitrites, carbonates, acetates, bicarbonates, hydroxides and oxides;
at least one catalyst, in an amount of 0.01 to 5% of the total mass of the composition;
at least one non-oxidizable polar solvent; and
at least one oxidizable multi-alkylated arylene compound with no two successive ring positions bearing alkyl group,
and
b. subjecting said composition to oxidation in the presence of an oxidizing agent selected from the group consisting of air and oxygen at a temperature of 100 to 250° C. and at a pressure of 10 to 60 bar to obtain aryl carboxylic acid,
said process resulting in the formation of less than 4000 ppm of partially oxidized derivatives of said multi-alkylated arylene compound; said derivatives comprising at least one carboxylic acid moiety and at least one aldehyde moiety.

The process is characterized by reduction in the thermo-oxidative loss of the ionic compound.

The oxidation is carried out in a continuous manner for a time period of at least 6 hours without the need of replenishment of the ionic compound.

The process further comprises a step of separating and recycling the ionic compound, the carboxylic acid solvent and the catalyst.

DETAILED DESCRIPTION

The inventors of the present disclosure focused on developing a composition containing ionic liquid/s which can be used in manufacturing aryl carboxylic acids such as terephthalic acid. After conducting several experiments and trials, the inventors particularly found that aryl alkyl ionic liquids can be used as a promoter in manufacturing aryl carboxylic acids such as terephthalic acid. Further, it was found that when aryl alkyl ionic liquids are used not only as a promoter but also as a co-solvent, there is enhancement in the reaction rate. Still further, it was found that when aryl alkyl ionic liquid is used as a promoter and as a co-solvent during the manufacture of aryl carboxylic acids such as terephthalic acid there is a significant reduction in formation of impurities such as 4-carboxy-benzaldehyde (4-CBA). The reason being the ionic liquid of the present disclosure is capable of solubilizing not only the terephthalic acid and 4-CBA but also various other intermediates and side products. It is advantageous to keep these intermediates in dissolved form in the ionic compounds, as they can be further oxidized into the desired product during the manufacture of terephthalic acid. Thus the concentration of intermediates can be reduced during the oxidation stage itself, thereby eliminating hydrogenation stage as against the conventional manufacturing process.

In accordance with the present disclosure there is provided a composition containing aryl alkyl ionic liquid for manufacturing aryl carboxylic acid. The aryl carboxylic acid includes but is not limited to terephthalic acid, isophthalic acid, p-toluic acid, m-toluic acid, 4-formyl benzoic acid, 3-formyl benzoic acid, Naphthoic acid, Trimesic acid, benzoic acid, substituted benzoic acid and combinations thereof.

The composition mainly consist of at least one ionic compound of Formula I; at least one catalyst comprising at least one metal selected from the group consisting of cobalt, magnesium, chromium, copper, nickel, vanadium, iron, molybdenum, tin, cerium, zirconium, cesium and titanium; at least one non-oxidizable polar solvent; and at least one oxidizable multi-alkylated arylene compound with no two successive ring positions bearing alkyl group. Typically, the non-oxidizable polar solvent includes but is not limited to acetic acid, methyl acetate, ethyl acetate, propyl acetate, benzyl acetate, water, combinations thereof and the like. The oxidizable multi-alkylated arylene compound includes but is not limited to para-xylene, meta-xylene, methylnaphthalene, mesitylene, toluene, substituted toluene and combinations thereof.

The Ionic liquid employed in the composition of the present disclosure is represented by the following Formula:

$$[Ar-Z-Q^{\oplus}-R]A^{\ominus} \qquad \text{Formula I}$$

wherein,

Ar is substituted or un-substituted aryl group,

Z is $(CH_2)_n$, wherein n is an integer from 0 to 10, $Q^+$ is an organic cation selected from the group consisting of quaternary ammonium, cholinium, sulfonium, phosphonium, guanidinium, imidazolium, pyridinium, pyrrolidinium, morpholinium, quinolinium, isoquinolium, pyrazolium and piperidinium, R is $C_1$ to $C_{20}$ linear or branched alkyl group or Ar—Z, $A^-$ is an anion selected from the group consisting of chlorides, bromides, fluorides, iodides, mesylates, tosylates, sulfates, alkyl sulfonates, phosphates, phosphonates, akyl phosphates, nitrates, nitrites, carbonates, acetates, bicarbonates, hydroxides and oxides;

In accordance with the present disclosure the composition contains a specific proportion of the ionic compound, the catalyst and the non-oxidizable polar solvent. The amount of the ionic compound is maintained between 0.05 and 50% of the total mass of the composition, whereas, the amount of the catalyst is maintained between 0.01 and 5% of the total mass of the composition. In accordance with the present disclosure the proportion of the ionic liquid to the non-oxidizable polar solvent is maintained between 1:1 and 1:20.

In accordance with the present disclosure the compound of formula I is selected from the group consisting of 1-benzyl, 3-methyl imidazolium chloride; 1-benzyl, 3-methyl imidazolium bromide; 1-benzyl, 3-methyl imidazolium acetate; 1-benzyl, 3-methyl imidazolium methane sulfonate; 1-benzyl, 3-methyl imidazolium phosphate; Benzyl tributyl phosphonium bromide; Benzyl tributyl ammonium bromide; 1-phenyl, 3-methyl imidazolium chloride; 1-phenyl, 3-methyl imidazolium bromide; 1-phenyl, 3-methyl imidazolium acetate; 1-phenyl, 3-methyl imidazolium methane sulfonate; 1-phenyl, 3-methyl imidazolium phosphate; Phenyl tributyl phosphonium bromide; Phenyl tributyl ammonium bromide; 1,3 di benzyl imidazolium chloride; 1,3 di benzyl imidazolium bromide; 1,3 di benzyl imidazolium acetate; 1,3 di benzyl imidazolium methane sulfonate; 1,3 di benzyl imidazolium phosphate; and combinations thereof.

In one embodiment the catalyst includes but is not limited to cobalt acetate, manganese acetate, cerium acetate, potassium acetate, cesium acetate, zirconium acetate, copper acetate, cobalt oxalate, manganese oxalate, cerium oxalate, potassium oxalate, cesium oxalate, zirconium oxalateand copper oxalate.

In one embodiment, Ar is phenyl, Z is $(CH_2)_n$, wherein n is 1, $Q^+$ is imidazolium group, R is methyl, $A^-$ is bromide and the compound of formula I is 1-benzyl, 3-methyl imidazolium bromide.

The composition of the present disclosure also includes at least one bromine source, as a promoter, which includes but is not limited to HBr, NaBr, KBr, $NH_4Br$, benzylbromide, monobromoacetic acid, di-bromo acetic acid, bromoacetyl bromide, tetrabromomethane and ethylene di-bromide.

In another embodiment there is provided a composition which contains at least one mono alkyl ionic liquid along with at least one aryl alkyl ionic liquid. Typically, the mono alkyl ionic liquid comprises an organic cation selected from the group consisting of quaternary ammonium, cholinium, sulfonium, phosphonium, guanidinium, imidazolium, pyridinium, pyrrolidinium, morpholinium, quinolinium, isoquinolium, pyrazolium and piperidinium; and an anion selected from the group consisting of chlorides, bromides, fluorides, iodides, mesylates, tosylates, sulfates, alkyl sulfonates, phosphates, phosphonates, akyl phosphates, nitrates, nitrites, carbonates, acetates, bicarbonates, hydroxides and oxides.

It is also found that the composition containing a combination of aryl alkyl ionic liquid and alkyl ionic liquid can also provide pure aryl carboxylic acid such as terephthalic acid by reducing the formation of impurities such as 4-carboxy-benzaldehyde (4-CBA).

The composition of the present disclosure when used in the preparation of aryl carboxylic acid, results in the formation of less than 4000 ppm of partially oxidized derivatives of said multi-alkylated arylene compound. The partially oxidized derivatives of said multi-alkylated arylene compound comprise at least one carboxylic acid moiety and at least one aldehyde moiety.

Typically, the partially oxidized derivative includes but is not limited to 4-carboxy benzaldehyde, 3-carboxy benzaldehyde, p-tolualdehyde, m-tolualdehyde, naphthalenecarboxaldehyde, 1,5-dicarboxilic, 3-formyl-benzene, benzaldehyde, substituted benzaldehyde and combination thereof.

In one embodiment the oxidizable multi-alkylated arylene compound is para-xylene, the non-oxidizable polar solvent is acetic acid, the partially oxidized derivative is 4-carboxy benzaldehyde and the aryl carboxylic acid is terephthalic acid.

The present disclosure also provides a process for obtaining aryl carboxylic acid. The aryl carboxylic acid includes but is not limited to terephthalic acid, isophthalic acid, p-toluic acid, m-toluic acid, 4-formyl benzoic acid, 3-formyl benzoic acid, Naphthoic acid, Trimesic acid, benzoic acid, substituted benzoic acid and combinations thereof.

The process mainly involves two steps. In the first step a composition comprising at least one ionic liquid of formula I, in an amount of 0.05 to 50% of the total mass of the composition;

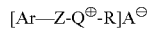  Formula I wherein,

Ar is substituted or un-substituted aryl group,

Z is $(CH_2)_n$, wherein n is an integer from 0 to 10, $Q^+$ is an organic cation selected from the group consisting of quaternary ammonium, cholinium, sulfonium, phosphonium, guanidinium, imidazolium, pyridinium, pyrrolidinium, morpholinium, quinolinium, isoquinolium, pyrazolium and piperidinium;

R is $C_1$ to $C_{20}$ linear or branched alkyl group or Ar—Z, $A^-$ is an anion selected from the group consisting of chlorides, bromides, fluorides, iodides, mesylates, tosylates, sulfates, alkyl sulfonatses, phosphates, phosphonates, akyl phosphates, nitrates, nitrites, carbonates, acetates, bicarbonates, hydroxides and oxides;

at least one catalyst, in an amount of 0.01 to 5% of the total mass of the composition; at least one non-oxidizable polar solvent; and at least one oxidizable multi-alkylated arylene compound with no two successive ring positions bearing alkyl group is prepared.

The non-oxidizable polar solvent employed in the process includes but is not limited to acetic acid, ethyl acetate, propyl acetate, benzyl acetate, benzyl acetate, water and the like. In the process of the present disclosure, the proportion of the ionic liquid to the non-oxidizable polar solvent is maintained between 1:1 and 1:20.

The oxidizable multi-alkylated arylene compound includes but is not limited to para-xylene, meta-xylene, methylnaphthalene, mesitylene, toluene, substituted toluene and combinations thereof.

In the second step, the obtained composition is subjected to oxidation in the presence an oxidizing agent selected from the group consisting of air and oxygen at a temperature of 100 to 250° C. and at a pressure of 10 to 60 bar to obtain aryl carboxylic acid. The process is characterized by the following features:

the formation of partially oxidized derivatives of said multi-alkylated arylene compound during the preparation of aryl carboxylic acid is less than 4000 ppm.

reduction in the thermo-oxidative loss of the ionic compound.

the oxidation is carried out in a continuous manner for a time period of at least 6 hours without the need of replenishment of the ionic compound.

In accordance with the present disclosure the partially oxidized derivative includes but is not limited to 4-carboxy benzaldehyde, 3-carboxy benzaldehyde, p-tolualdehyde, m-tolualdehyde, naphthalenecarboxaldehyde, 1,5-dicarboxilic, 3-formyl-benzene, benzaldehyde, substituted benzaldehyde and combinations thereof.

In accordance with the present disclosure the ionic liquid of formula I includes but is not limited to 1-benzyl, 3-methyl imidazolium chloride; 1-benzyl, 3-methyl imidazolium bromide; 1-benzyl, 3-methyl imidazolium acetate; 1-benzyl, 3-methyl imidazolium methane sulfonate; 1-benzyl, 3-methyl imidazolium phosphate; Benzyl tributyl phosphonium bromide; Benzyl tributyl ammonium bromide; 1-phenyl, 3-methyl imidazolium chloride; 1-phenyl, 3-methyl imidazolium bromide; 1-phenyl, 3-methyl imidazolium acetate; 1-phenyl, 3-methyl imidazolium methane sulfonate; 1-phenyl, 3-methyl imidazolium phosphate; Phenyl tributyl phosphonium bromide; Phenyl tributyl ammonium bromide; 1,3 di benzyl imidazolium chloride; 1,3 di benzyl imidazolium bromide; 1,3 di benzyl imidazolium acetate; 1,3 di benzyl imidazolium methane sulfonate; 1,3 di benzyl imidazolium phosphate; and combinations thereof. In one embodiment, Ar is phenyl, Z is $(CH_2)_n$, wherein n is 1, $Q^+$ is imidazolium group, R is methyl, and $A^-$ is bromide.

The process of the present disclosure also involves incorporation of at least one bromine source selected from the group consisting of HBr, NaBr, KBr, $NH_4Br$, benzylbromide, monobromoacetic acid, di-bromo acetic acid, bromoacetyl bromide, tetrabromomethane and ethylene di-bromide in said composition.

In another embodiment the process further comprises incorporation of at least one mono alkyl ionic liquid comprising an organic cation selected from the group consisting of quaternary ammonium, cholinium, sulfonium, phosphonium, guanidinium, imidazolium, pyridinium, pyrrolidinium, morpholinium, quinolinium, isoquinolium, pyrazolium and piperidinium; and an anion selected from the group consisting of chlorides, bromides, fluorides, iodides, mesylates, tosylates, sulfates, alkyl sulfonates, phosphates, phosphonates, akyl phosphates, nitrates, nitrites, carbonates, acetates, bicarbonates, hydroxides and oxides in said composition.

The process of the present disclosure also involves a step of separating and recycling the ionic compound, the carboxylic acid solvent and the catalyst.

In one embodiment there is provided a process for the preparation of terephthalic acid. In the first step, a composition comprising at least one ionic liquid of Formula I; at least one catalyst; acetic acid; and para-xylene is prepared. In the second step, the obtained composition is subjected to oxidation in the presence of an oxidizing agent at a temperature of 100 to 250° C. and at a pressure of 10 to 60 bar to obtain terephthalic acid. It is found that the formation of 4-carboxy benzaldehyde (4-CBA) during the preparation of aryl carboxylic acid is less than 4000 ppm.

The following examples illustrate the disclosure. The examples used herein are intended merely to facilitate an understanding of the ways in which the embodiments herein may be practiced and to further enable those of skill in the art to practice the embodiments herein. Accordingly, the examples should not be construed as limiting the scope of the embodiments herein.

EXAMPLES

Example 1

Thermal Stability Testing Alkyl Ionic Liquid

Thermal stability of 1-butyl, 3-methyl imidazolium chloride in the presence of air was studied at different temperatures at 20 bar pressure in a high pressure slurry reactor made of titanium. It was found that at 140° C., there was a drastic uptake of oxygen. The sample was taken out and tested. It was found that it decomposed.

Example 2

Thermal Stability Testing Aryl Alkyl Ionic Liquid

Example 1 was repeated using 1-benzyl, 3-methyl imidazolium chloride in place of 1-butyl, 3-methyl imidazolium chloride. Decomposition onset temperature was found to be 180° C. for this ionic salt.

Example 3

Preparation of Terephthalic Acid

Oxidation of p-xylene was carried out using acetic acid as a solvent by using cobalt acetate and manganese acetate as catalyst in the presence of 1-butyl, 3-methyl imidazolium bromide (550 ppm) as a promoter at 180° C. temperature and 20 bar pressure for 3 hours reaction time. The 4-CBA content in terephthalic acid was 15000 ppm.

Example 4

Preparation of Terephthalic Acid

Oxidation of p-xylene was carried out using acetic acid as a solvent by using cobalt acetate and manganese acetate as catalyst in the presence of 1-benzyl, 3-methyl imidazolium bromide (4%) as a promoter and as well as a co-solvent at 215° C. temperature and 40 bar pressure for 3 hours reaction time. The 4-CBA content in terephthalic acid was 3100 ppm.

Example 5

Preparation of Terephthalic Acid

Oxidation of p-xylene was carried out using acetic acid as a solvent by using cobalt acetate and manganese acetate as catalyst in the presence of 1-benzyl, 3-methyl imidazolium bromide (4%) as a promoter and as well as a co-solvent and 20% of 1-butyl, 3-methyl imidazolium acetate at 215° C. temperature and 40 bar pressure for 3 hours reaction time. The 4-CBA content in terephthalic acid was 4800 ppm.

Example 6

Preparation of Benzoic Acid from Toluene

Oxidation of Toluene was carried out using acetic acid as a solvent by using cobalt acetate and manganese acetate as catalyst in the presence of 1-benzyl, 3-methyl imidazolium bromide (4%) as a promoter and as well as a co-solvent at 150° C. temperature and 40 bar pressure for 3 hours reaction time. Benzaldehyde was formed as a partially oxidized derivative.

Example 7

Preparation of Isophthalic Acid from m-Xylene

Oxidation of m-xylene was carried out using acetic acid as a solvent by using cobalt acetate and manganese acetate as catalyst in the presence of 1-benzyl, 3-methyl imidazolium bromide (4%) as a promoter and as well as a co-solvent at 215° C. temperature and 40 bar pressure for 3 hours reaction time. 3-Toluic acid and 3-carboxybenzaldehyde (3-CBA) were formed as partially oxidized derivatives.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "a", "at least" or "at least one" suggests the use of one or more elements or ingredients or quantities, as the use may be in the embodiment of the disclosure to achieve one or more of the desired objects or results.

The numerical values given for various physical parameters, dimensions and quantities are only approximate values and it is envisaged that the values higher or lower than the numerical value assigned to the physical parameters, dimensions and quantities fall within the scope of the disclosure and the claims unless there is a statement in the specification to the contrary.

While certain embodiments of the disclosure have been described, these embodiments have been presented by way of examples only, and are not intended to limit the scope of the disclosure. Variations or modifications in the composition of this disclosure, within the scope of the disclosure, may occur to those skilled in the art upon reviewing the disclosure herein. Such variations or modifications are well within the spirit of this disclosure.

The invention claimed is:

1. A composition for preparing aryl carboxylic acid; said composition comprising:
   i. at least one ionic liquid of formula I, in an amount of 0.05 to 50% of the total mass of the composition;

wherein,
   Ar is substituted or un-substituted aryl group,
   Z is $(CH_2)_n$, wherein n is an integer from 0 to 10,
   $Q^+$ is an organic cation selected from the group consisting of quaternary ammonium, cholinium, sulfonium, phosphonium, guanidinium, imidazolium, pyridinium, pyrrolidinium, morpholinium, quinolinium, isoquinolium, pyrazolium and piperidinium;
   R is $C_1$ to $C_{20}$ linear or branched alkyl group or Ar—Z,
   $A^-$ is an anion selected from the group consisting of chlorides, bromides, fluorides, iodides, mesylates, tosylates, sulfates, alkyl sulfonates, phosphates phosphonates, akyl phosphates, nitrates, nitrites, carbonates, acetates, bicarbonates, hydroxides and oxides;
   ii. at least one catalyst, in an amount of 0.01 to 5% of the total mass of the composition;
   iii. at least one non-oxidizable polar solvent; and
   iv. at least one oxidizable multi-alkylated arylene compound with no two successive ring positions bearing alkyl group,
   said composition when used in the preparation of aryl carboxylic acid results in the formation of less than 4000 ppm of partially oxidized derivatives of said multi-alkylated arylene compound; said derivatives comprising at least one carboxylic acid moiety and at least one aldehyde moiety.

2. The composition as claimed in claim 1, wherein the proportion of the ionic liquid to the non-oxidizable polar solvent ranges between 1:1 and 1:20.

3. The composition as claimed in claim 1, wherein the catalyst comprises at least one metal compound, the metal being selected from the group consisting of cobalt, magnesium, chromium, copper, nickel, vanadium, iron, molybdenum, tin, cerium, zirconium, cesium and titanium.

4. The composition as claimed in claim 1, wherein the catalyst is at least one selected from the group consisting of cobalt acetate, manganese acetate, cerium acetate, potassium acetate, cesium acetate, zirconium acetate, copper acetate, cobalt oxalate, manganese oxalate, cerium oxalate, potassium oxalate, cesium oxalate, zirconium oxalate and copper oxalate.

5. The composition as claimed in claim 1, wherein the non-oxidizable polar solvent is at least one solvent selected from the group consisting of acetic acid, methyl acetate, ethyl acetate, propyl acetate, benzyl acetate and water.

6. The composition as claimed in claim 1, wherein Ar is phenyl, Z is $(CH_2)_n$, wherein n is 1, $Q^+$ is imidazolium group, R is methyl, and $A^-$ is bromide.

7. The composition as claimed in claim 1, further comprises at least one mono alkyl ionic liquid comprising an organic cation selected from the group consisting of quaternary ammonium, cholinium, sulfonium, phosphonium, guanidinium, imidazolium, pyridinium, pyrrolidinium, morpholinium, quinolinium, isoquinolium, pyrazolium and piperidinium; and an anion selected from the group consisting of chlorides, bromides, fluorides, iodides, mesylates, tosylates, sulfates, alkyl sulfonates, phosphates, phosphonates, akyl phosphates, nitrates, nitrites, carbonates, acetates, bicarbonates, hydroxides and oxides.

8. The composition as claimed in claim 1, wherein the aryl carboxylic acid is at least one compound selected from the group consisting of terephthalic acid, isophthalic acid, p-toluic acid, m-toluic acid, 4-formyl benzoic acid, 3-formyl benzoic acid, Naphthoic acid, Trimesic acid, benzoic acid and substituted benzoic acid.

9. The composition as claimed in claim 1, wherein the oxidizable multi-alkylated arylene compound is at least one selected from the group consisting of para-xylene, meta-xylene, methylnaphthalene, mesitylene, toluene and substituted toluene.

10. The composition as claimed in claim 1, wherein the partially oxidized derivative is at least one selected from the group consisting of 4-carboxy benzaldehyde, 3-carboxy benzaldehyde, p-tolualdehyde, m-tolualdehyde, naphthalenecarboxaldehyde, 1,5-dicarboxilic, 3-formyl-benzene, benzaldehyde and substituted benzaldehyde.

11. The composition as claimed in claim 1, wherein the oxidizable multi-alkylated arylene compound is para-xylene, the non-oxidizable polar solvent is acetic acid, the partially oxidized derivative is 4-carboxy benzaldehyde and the aryl carboxylic acid is terephthalic acid.

12. A process for obtaining aryl carboxylic acid; said process comprising the following steps:
preparing a composition comprising:
i. at least one ionic liquid of formula I, in an amount of 0.05 to 50% of the total mass of the composition;

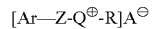

Formula I wherein,
Ar is substituted or un-substituted aryl group,
Z is $(CH_2)_n$, wherein n is an integer from 0 to 10,
$Q^+$ is an organic cation selected from the group consisting of quaternary ammonium, cholinium, sulfonium, phosphonium, guanidinium, imidazolium, pyridinium, pyrrolidinium, morpholinium, quinolinium, isoquinolium, pyrazolium and piperidinium;
R is $C_1$ to $C_{20}$ linear or branched alkyl group or Ar—Z,
$A^-$ is an anion selected from the group consisting of chlorides, bromides, fluorides, iodides, mesylates, tosylates, sulfates, alkyl sulfonatses, phosphates, phosphonates, akyl phosphates, nitrates, nitrites, carbonates, acetates, bicarbonates, hydroxides and oxides;
ii. at least one catalyst, in an amount of 0.01 to 5% of the total mass of the composition;
iii. at least one non-oxidizable polar solvent; and
iv. at least one oxidizable multi-alkylated arylene compound with no two successive ring positions bearing alkyl group,
and
subjecting said composition to oxidation in the presence of an oxidizing agent selected from the group consisting of air and oxygen at a temperature of 100 to 250° C. and at a pressure of 10 to 60 bar to obtain aryl carboxylic acid,
said process resulting in the formation of less than 4000 ppm of partially oxidized derivatives of said multi-alkylated arylene compound; said derivatives comprising at least one carboxylic acid moiety and at least one aldehyde moiety.

13. The process as claimed in claim 12, wherein said process is characterized in that the oxidation is carried out in a continuous manner for a time period of at least 6 hours without replenishing the ionic compound.

* * * * *